United States Patent [19]

Cookson et al.

[11] 4,203,907

[45] May 20, 1980

[54] PROCESS FOR PREPARING A FURANIC COMPOUND

[75] Inventors: Richard C. Cookson, Southampton, England; Karl-Heinrich Schulte-Elte, Onex; Arnold Hauser, Petit-Lancy, both of Switzerland

[73] Assignee: Firmenich, S.A., Geneva, Switzerland

[21] Appl. No.: 919,484

[22] Filed: Jun. 27, 1978

[30] Foreign Application Priority Data

Jun. 28, 1977 [CH] Switzerland .......................... 7902/77

[51] Int. Cl.$^2$ ............................................ C07D 307/38
[52] U.S. Cl. ............................. 260/346.11; 260/347.4; 260/347.5; 260/347.8

[58] Field of Search ............. 260/346.11, 347.4, 347.5, 260/347.8

[56] References Cited

U.S. PATENT DOCUMENTS 3,892,782  7/1975  Buchi .............................. 260/346.11

Primary Examiner—Richard Raymond
Attorney, Agent, or Firm—Scully, Scott, Murphy & Presser

[57] ABSTRACT

Process for preparing 3-methyl-2-[3-methyl-but-2-en-1-yl]-furan, known under the trivial name of rosefuran, starting from cheaply available furfural via a four-step synthesis.

7 Claims, No Drawings

PROCESS FOR PREPARING A FURANIC COMPOUND

BACKGROUND OF THE INVENTION

As a result of an analytical investigation on Bulgarian rose oil (Rosa Damascena Mill.), E. sz. Kovats could determine for the first time the presence therein of a furan derivative of formula

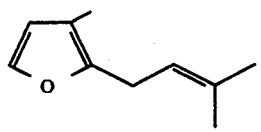

(I), 3-methyl-2-[3-methyl-but-2-en-1-yl]-furan, known ever since under the name of "rosefuran". The first total synthesis of this compound was realized by G. Büchi et al. [see: J. Org. Chem., 33, 1227(1968)] by making use of 3-methyl-2-furoic acid according to the hereinbelow illustrated process:

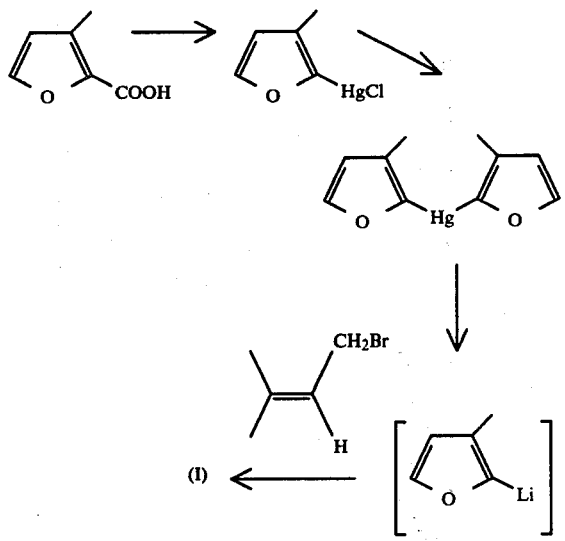

More recently [see: O. P. Vig et al., J. Indian Chem.-Soc., 51, (10), 900–2 (1974)], rosefuran has been synthesized starting from 3-furylmethanol according to the following reaction scheme:

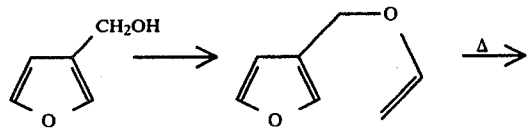

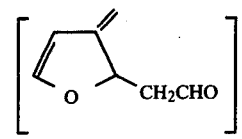

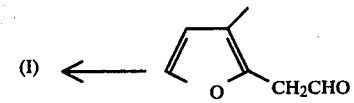

Though interesting they may be from the academic viewpoint, the two above mentioned processes are particularly unsatisfactory whenever applied to the industrial large scale preparation of rosefuran, their main disadvantage being represented by the high price of the required starting materials.

In view of the usefulness presented by rosefuran, the perfume industry has constantly shown a lively interest to its synthesis; sofar however without any success.

THE INVENTION

We have now discovered that 3-methyl-2-[3-methyl-but-2-en-1-yl]-furan can be conveniently prepared by a novel process which consists in the following subsequent steps:

(a) adding a 2-methyl-prop-2-en-1-yl magnesium halide to furfural to yield 2-[1-hydroxy-3-methyl-but-3-en-1-yl]-furan;

(b) reacting the thus obtained carbinol with an alkyl orthoacetate in the presence of a catalyst selected from the group consisting of carboxylic acids or an organic protonic acid having a $pK_a$ of about 7 to 9 to give an alkyl 2-[3-methyl-but-3-en-1-ylidene]-2,3-dihydro-furylacetate;

(c) treating said ester with an acidic agent to give an alkyl 2-[3-methyl-but-2-en-1-yl]-furyl-acetate, and (d) hydrolyzing and then decarboxylating the obtained alkyl furyl-acetate; or (c') hydrolyzing and then decarboxylating the alkyl 2-[3-methyl-but-3-en-1-ylidene]-2,3-dihydro-furyl acetate obtained in accordance with letter (b) above and (d') isomerizing the terminal double bond of 3-methyl-2-[3-methyl-but-3-en-1-yl]-furan by means of a thermal treatment of this latter compound in the presence of palladium on charcoal.

The process of the invention can be illustrated by the following reaction scheme

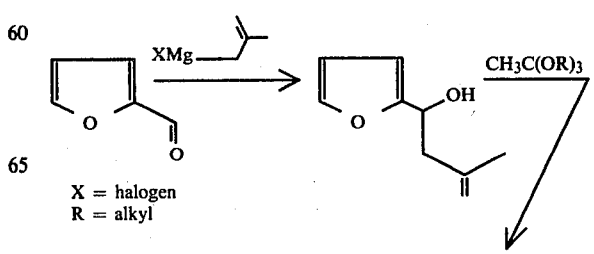

X = halogen
R = alkyl

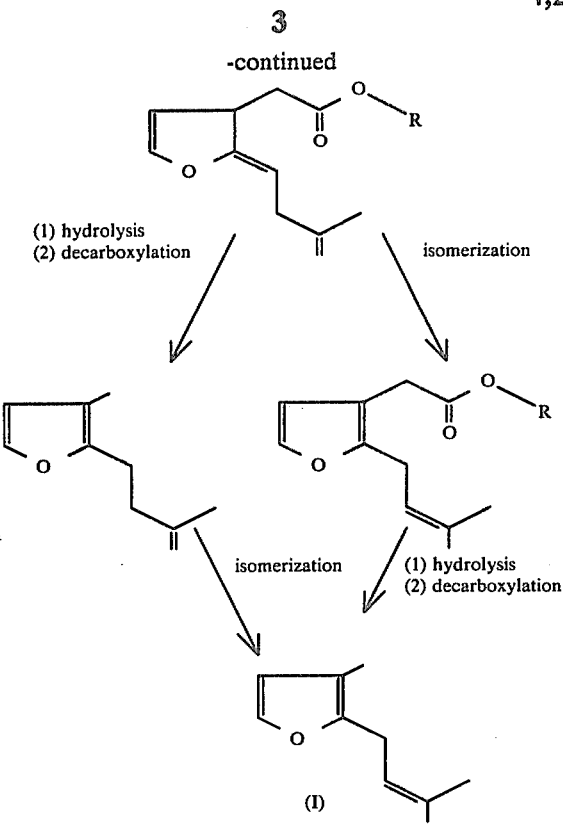

PREFERRED EMBODIMENTS OF THE INVENTION

According to a preferred embodiment of the invention, step (a), which consists in an addition according to the Grignard type reaction, is effected by 2-methyl-prop-2-en-1-yl magnesium chloride.

The reaction of the obtained carbinol with an alkyl ortho-acetate, viz. a trialkyl ortho-acetate, is carried out by making use of triethyl or trimethyl orthoacetate, both of these reactants being currently available on the market at low price. This step of the process of the invention formally constitutes a Claisen type rearrangement. The presence of an acid catalyst is essential for the good course of the reaction and, for this purpose, it is made use of a carboxylic acid such as propionic [see e.g. Tetrahedron Letters, 691 (1975)] or dimethylpropionic (pivalic) acid or of an organic acid having a dissociation constant, as defined in an aqueous medium, of between about 7 and 9 ($pK_a$ values).

According to a preferred embodiment of the invention, typical organic acids include phenol derivatives, such as e.g. o-nitro-phenol, m-nitro-phenol, p-nitro-phenol, o-chloro-phenol, m-chloro-phenol or o-hydroxy-acetophenone. o-Nitro-phenol is preferred.

The utilized proportions of said ortho-esters can vary very widely; however, for reason of economy, preferred proportions are of from about 2 to 4 equivalents of said ortho-esters per 1 equivalent of 2-[1-hydroxy-3-methyl-but-3-en-1-yl]-furan.

The reaction which characterizes step (b) of the process is carried out at a temperature comprised within wide limits. For practical reasons the said reaction is effected at a temperature near the boiling point of the treated mixture, preferably at a temperature slightly lower than said boiling point. Thus, by making use of triethyl ortho-acetate, good yields of end product were obtained by operating at a temperature of from about 125° to 150° C. At such a temperature ethanol and ethyl acetate were collected by distillation as soon as formed in the reaction mixture.

Step (c) of the process of the invention, which namely consists in the concomitant isomerization of the two ethylenic double bonds of the alkenylidene sidechain of the alkyl furyl-acetate obtained in accordance with letter (b), is carried out by means of an acidic isomerizing agent, such as a strong organic acid, e.g. p-toluene-sulphonic acid, an acidic diatomaceous earth or an acidic cations exchange resin.

The subsequent steps of hydrolysis and decarboxylation are effected according to usual techniques, namely by hydrolyzing the obtained alkyl furyl-acetate with an aqueous base, which hydrolysis is followed by a thermal treatment of the reaction mixture at a temperature of about 180° to 220° C., preferably at 190°–210° C.

In accordance with a modification of the process of the present invention, the sequence of steps (c) and (d) can be inverted according to (c') and (d'). In this case the isomerization is carried out by thermally treating 3-methyl-2-[3-methyl-but-3-en-1-yl]-furan in the presence of palladium on charcoal, e.g. at 10%, in a nitrogen atmosphere enriched with hydrogen.

The preferred volume ratio between the two gases is approximately 9.5:0.5 (nitrogen:hydrogen). The isomerization is effected in an organic solvent such as isopropyl acetate and at a temperature of 80° to 120° C., preferably of 90° to 110° C. Such an isomerization is particularly specific and enables the formation of the desired isomer almost exclusively, which isomer was accompanied by traces of 3-methyl-2-[3-methyl-but-1-en-1-yl]-furan and by minor quantities of 3-methyl-2-[3-methyl-butyl]-furan. The desired isomer could be however readily isolated from the obtained reaction mixture.

The invention is illustrated by but not limited to the following example wherein the temperatures are indicated in degrees centigrade.

EXAMPLE

3-Methyl-2-[3-methyl-but-2-en-1-yl]-furan a. 2-[1-hydroxy-3-methyl-but-3-en-1-yl]-furan Two ethereal solutions of 2-methyl-prop-2-en-1-yl chloride (135 g; 1.5 mole) and, respectively, furfural (96 g; 1.0 mole), each in 500 ml of anhydrous diethyl ether, were simultaneously added under stirring to a suspension of 34 g of magnesium turnings (1.5 mole) in 100 ml of ether. The magnesium suspension was preliminarly activated with some drops of methyl iodide.

The addition was effected under a nitrogen atmosphere while the reaction mixture was kept at about 25°–30° by external cooling, then at room temperature for 2–3 h.

After cooling to 5°–10°, the mixture was hydrolyzed with ca. 1 l of a 20% aqueous solution of ammonium chloride, then extracted with 3 fractions of 300 ml each of ether. The combined organic extracts were washed, dried over $Na_2SO_4$ and evaporated to dryness, whereupon the residue was fractional distilled under reduced pressure to yield 123 g (yield 81%) of the desired product.

Bp. 64°–65°/8 Torr.

IR: 3350, 3110, 3070, 1645, 1505 and 900 $cm^{-1}$;

NMR($CCl_4$): 1.69 (3H, s); 2.48 (2H, d, J=7 Hz); 2.56 (1H, s); 4.75 (3H, m); 6.2 (2H, m); 7.28 (1H, d, J=2 Hz) δ ppm;

MS: M+ =152 (<1); m/e: 134 (1); 119 (1); 105 (1); 97 (100); 69 (4); 41 (16).

b. ethyl-2-[3-methyl-but-3-en-1-ylidene]-2,3-dihydrofuryl-acetate

A solution of 60.8 g (0.4 mole) of the carbinol obtained according to letter (a) above, 11.1 g (0.08 mole) of o-nitro-phenol and 194.4 g (1.2 mole) of triethyl ortho-acetate were slowly heated during 8–10 h to 145°–150° under nitrogen atmosphere while stirring. Meanwhile, ethanol and ethyl acetate formed in the course of the reaction were gradually distilled off whereas the excess of triethyl ortho-acetate was recovered by vacuum distillation. The thus obtained residue was dissolved in petrol ether (b.p. 30°–50°) and the resulting solution was washed with 5% aqueous NaOH, dried over $Na_2SO_4$ and finally evaporated. 46.6 g (yield 52.5%) of the title ethyl furyl-acetate were obtained by fractional distillation. Purity ca. 35%; b.p. 65°–70°/0.2 Torr.

IR(film): 3110, 3075, 1740, 1650, 1620 and 900 cm$^{-1}$;
NMR($CCl_4$): 1.28 (3H, t, J=7 Hz); 1.74 (3H, s); 2.42 (2H, d, J=7 Hz); 2.77 (2H, d, J=7 Hz); 4.11 (2H, q, J=7 Hz); 4.66 (2H, s); 5.19 (1H, t, J=3 Hz); 6.43 (1H, s) δ ppm;
MS: M+ =222 (18); m/e: 207 (2), 193 (15), 176 (7), 167 (100), 149 (7), 135 (34), 121 (23), 107 (15), 95 (72), 79 (16), 67 (6), 55 (19), 41 (15).

c. ethyl-2-[3-methyl-but-2-en-1-yl]-furyl-acetate

A solution of 6.66 (30 mmole) of the ester obtained sub letter (d) above, and 0.54 g (3 mmole) of p-toluenesulphonic acid mono-hydrate in 60 ml of toluene were heated under nitrogen at 60° during about 15 h. After cooling the solution was poured onto ice and diluted with an aqueous sodium bicarbonate solution, then extracted with two fractions of 50 ml each of ether. The combined organic extracts were washed, dried, evaporated and finally distilled. 3.71 g (yield 55.7%) of the desired ester were thus collected.

B.p. 66°–7°/0.1 Torr;
IR(film): 1740 and 1520 cm$^{-1}$;
NMR($CCl_4$): 1.24 (3H, t, J=7 Hz); 1.72 (6H, s); 3.23 (2H, s); 3.27 (2H, d, J=7 Hz); 4.09 (2H, q, J=7 Hz); 5.2 (1H, t); 6.19 (1H, d, J=2 Hz); 7.24 (1H, d, J=7 Hz) δ ppm.

c'. 3-methyl-2-[3-methyl-but-3-en-1-yl]-furan 30 ml of a 1 N NaOH solution in ethanol were added to a boiling solution of 6.66 g (30 mmole) of the ester obtained in accordance with letter (b) above in 150 ml of 80% ethanol. Saponification was completed in about 5 h, whereupon 300 g of ice were added to the reaction mixture before extraction with two fractions of 100 ml each of petrol-ether.

The cooled aqueous phase was acidified with 1 N HCl, saturated with NaCl and extracted with 3 fractions of 100 ml each of ether. The combined extracts were washed, dried over $Na_2SO_4$ and evaporated to dryness. The obtained acid (5.79 g) was directly decarboxylated by heating it at 200°–240° over an oil bath. By distillation under reduced pressure at 300–500 Torr there was obtained 3.19 g (yield 71%) of 3-methyl-2-[3-methyl-but-3-en-1-yl]-furan (isorosefuran). This compound could be obtained by collecting it as formed in the course of the decarboxylation (reaction time: ca. 5 h).

IR: 3080, 1640, 1625, 1575, 1510, 885 and 725 cm$^{-1}$;
NMR: 1.71 (3H, m); 1.92 (3H, s); 2.2–2.8 (4H, m); 4.65 (2H, m); 6.01 and 7.09 (twice 1 d, J≈2 Hz) δ ppm;
MS: 150 (10); m/e: 135 (0.1), 67 (7), 55 (3), 41 (14).

d'. 3-methyl-2-[3-methyl-but-2-en-1-yl]-furan 3.19 g of iso-rosefuran obtained in accordance with letter (c') above, were added to a suspension of about 0.5 g of 10% palladium on charcoal in 60 ml of isopropyl acetate in a 95:5 nitrogen:hydrogen atmosphere and the reaction mixture was heated at about 90°–95°. Once the reaction was over (reaction time of about 5 h), the desired compound was separated by distillation (yield ca. 90%). The analytical characters of the obtained rosefuran was in all respects identical to those of an analytical sample prepared in accordance with known methods.

d. 3-methyl-2-[3-methyl-but-2-en-1-yl]-furan

By carrying out the reaction of saponification and decarboxylation, as described sub letter (c') above, on ethyl 2-[3-methyl-but-2-en-1-yl]-furyl-acetate, rosefuran was obtained in a 82% yield. The obtained mixture contained about 10% by weight of iso-rosefuran.

The above described process step (b.) could be modified by making use of pivalic acid as acid catalyst according to the following:

b(modified). methyl-2-[3-methyl-but-3-en-1-ylidene]-2,3-dihydrofuryl-acetate

A solution of 152 g (1 mole) of the carbinol, obtained according to letter (a.) above, in 360 g (3 mole) of methyl ortho-acetate was heated to 120° under stirring then treated during two days (twice 8 hours) with 20 g of pivalic acid in 50 g of methyl ortho-acetate, which acid solution was added dropwise. Methanol and the excess methyl ortho-acetate were distilled off as formed. The temperature was slowly increased from 120° to 130° during the first day of reaction and to 135° in the second day, whereas during the last 2 or 3 hours of reaction it was brought to 140°–145°. Under these conditions about one half of the orthoester was taken off while the remaining quantity was eliminated under reduced pressure (20–30 Torr). The residual product was subjected to the subsequent reaction step of hydrolysis in much the same way as indicated sub. letter (c) above.

What we claim is:

1. A process for the preparation of 3-methyl-2-[3-methyl-but-2-en-1-yl]-furan which comprises the following subsequent steps:
    (a) adding a 2-methyl-prop-2-en-1-yl magnesium halide to furfural to yield 2-[1-hydroxy-3-methyl-but-3-en-1-yl]-furan;
    (b) reacting the thus obtained carbinol with an alkyl ortho-acetate in the presence of a catalyst selected from the group consisting of carboxylic acids or an organic protonic acid having a $pK_a$ of about 7 to 9 to give an alkyl 2-[3-methyl-but-3-en-1-ylidene]-2,3-dihydro-furyl-acetate;
    (c) treating said ester with an acidic agent to given an alkyl 2-[3-methyl-but-2-en-1-yl]-furyl-acetate, and
    (d) hydrolyzing and then decarboxylating the obtained alkyl furyl-acetate;
    or
    (c') hydrolyzing and then decarboxylating the alkyl 2-[3-methyl-but-3-en-1-ylidene]-2,3-dihydro-furyl acetate obtained in accordance with letter (b) above and (d') isomerizing the terminal double bond of 3-methyl-2-[3-methyl-but-3-en-1-yl]-furan by means of a thermal treatment of this latter compound in the presence of palladium on charcoal.

2. Process according to claim 1 wherein 2-methyl-prop-2-en-1-yl magnesium chloride is added to furfural.

3. Process according to claim 1 wherein the alkyl ortho-acetate is trimethyl or triethyl ortho-acetate.

4. Process according to claim 1 wherein the carbinol obtained sub letter (a.) is treated with triethyl or trimethyl ortho-acetate in the presence of o-nitrophenol or pivalic acid.

5. Process according to claim 4 wherein the reaction is carried out at a temperature of about 125°–150° C.

6. Process according to claim 1 wherein the isomerization of the terminal double bond of 3-methyl-2-[3-methyl-but-3-en-1-yl]-furan is effected by means of a thermal treatment in the presence of palladium on charcoal in a nitrogen atmosphere enriched with hydrogen.

7. Process according to claim 6 wherein the reaction is carried out at a temperature of about 80° to 120° C. in an inert organic solvent.